US012784378B2

(12) United States Patent
Henry et al.

(10) Patent No.: US 12,784,378 B2
(45) Date of Patent: Nov. 3, 2026

(54) MIXED REALITY NAVIGATION OPERATING METHOD, SYSTEM, AND PROGRAM FOR ASSISTING SHOULDER PROSTHESIS INSTALLATION

(71) Applicant: PIXEE MEDICAL, Besançon (FR)

(72) Inventors: Sébastien Henry, La Crau (FR); Romain Fissette, Besançon (FR); Anthony Agustinos, Devecey (FR)

(73) Assignee: PIXEE MEDICAL, Besançon (FR)

( * ) Notice: Subject to any disclaimer, the term of this patent is extended or adjusted under 35 U.S.C. 154(b) by 302 days.

(21) Appl. No.: 18/613,815

(22) Filed: Mar. 22, 2024

(65) Prior Publication Data

US 2024/0331318 A1 Oct. 3, 2024

Related U.S. Application Data

(60) Provisional application No. 63/493,249, filed on Mar. 30, 2023.

(51) Int. Cl.
*G06T 19/00* (2011.01)
*A61B 34/10* (2016.01)
(Continued)

(52) U.S. Cl.
CPC ............ *G06T 19/006* (2013.01); *A61B 34/10* (2016.02); *A61B 90/361* (2016.02); *G06T 19/20* (2013.01); *A61B 2034/105* (2016.02); *A61B 2090/365* (2016.02); *G06T 2219/2004* (2013.01); *G06T 2219/2016* (2013.01)

(58) Field of Classification Search
None
See application file for complete search history.

(56) References Cited

U.S. PATENT DOCUMENTS

2008/0269596 A1* 10/2008 Revie .................... A61B 90/39 705/28
2013/0245461 A1* 9/2013 Maier-Hein ......... A61B 90/361 600/476

(Continued)

OTHER PUBLICATIONS

Zimmer Biomet, "Trabecular Metal(TM) Reverse Shoulder System Surgical Technique", Warsaw, IN, 2017, pp. 1-48 (total 50 pages).

(Continued)

*Primary Examiner* — Ryan M Gray
(74) *Attorney, Agent, or Firm* — Seckel IP, PLLC

(57) ABSTRACT

The method of performing an operation on a body part of a patient uses a mixed reality (MR) device worn by the user. A visual representation of an operating scene includes a virtual anatomical feature representing an actual anatomical feature of the patient. A position and/or orientation of the visual representation relative to the anatomical feature of the patient is first adjusted to be superposed with the anatomical feature of the patient. The visual representation is displayed by the MR device superposed with the anatomical feature of the patient in a field of vision of the user. The position and/or orientation of the visual representation is repeatedly or continuously adjusted, so that, when the MR device moves relative to the anatomical feature of the patient, the visual representation remains superposed with the anatomical feature of the patient.

19 Claims, 5 Drawing Sheets

(51) Int. Cl.
*A61B 90/00* (2016.01)
*G06T 19/20* (2011.01)

(56) References Cited

U.S. PATENT DOCUMENTS

| | | | | |
|---|---|---|---|---|
| 2013/0267838 | A1* | 10/2013 | Fronk | A61B 5/064 600/424 |
| 2019/0380792 | A1* | 12/2019 | Poltaretskyi | G06N 3/08 |
| 2022/0079675 | A1* | 3/2022 | Lang | G02B 30/52 |
| 2022/0125519 | A1* | 4/2022 | Slagmolen | A61B 34/10 |
| 2022/0151705 | A1* | 5/2022 | Nikou | G09B 23/28 |
| 2024/0331318 | A1* | 10/2024 | Henry | A61B 34/10 |
| 2024/0374313 | A1* | 11/2024 | Dorman | A61B 34/10 |

OTHER PUBLICATIONS

Gregory et al., “Les causes du descellement aseptique des prothèses totales anatomiques de l’épaule” [“The causes of aseptic loosening of anatomical total shoulder prostheses”], e-memoires de l’Académie de Chirurgie [e-memoirs of the National Academy of Surgery], 2015, vol. 14, No. 2, pp. 7-12 (with English translation; total 12 pages).

Iannotti et al, “Three-dimensional preoperative planning software and a novel information transfer technology improve glenoid component positioning”, Journal of Bone Joint Surgery, Incorporated, 2014, vol. e71, pp. 1-8.

Greene et al., “Navigated versus non-navigated results of a CT-based computer-assisted shoulder arthroplasty system in 30 cadavers”, Orthopedic Proceedings, 2019, vol. 101-B(SUPP_5), pp. 23-23 (English abstract, total 2 pages).

Arthrex, “Virtual Implant Positioning(TM) (VIP) Glenoid Targeter Surgical Technique”, Naples, FL, 2020, pp. 1-8.

Stryker, “TrueSight(R) Personalized Planning & Targeting System Operative Technique”, Kalamazoo, MI, 2019, pp. 1-16.

Exatech, “Shoulder Operative Technique”, Gainesville, FL, 2018, pp. 1-48 (total 50 pages).

Greene et al., “Clinical use of computer assisted anatomic total shoulder arthroplasty system: an analysis of 574 cases”, EPiC Series in Health Sciences, 2019, vol. 3, pp. 147-151.

Greene et al., “Clinical use of computer assisted anatomic total shoulder arthroplasty system: an analysis of 1702 cases”, EPiC Series in Health Sciences, 2019, vol. 3, pp. 152-156.

Suroto et al., “Morphology of humeral head and glenoid in normal shoulder of Indonesian population”, Orthopedic Research and Reviews, 2022, vol. 14, pp. 459-469.

* cited by examiner

MIXED REALITY NAVIGATION OPERATING METHOD, SYSTEM, AND PROGRAM FOR ASSISTING SHOULDER PROSTHESIS INSTALLATION

CROSS-REFERENCE TO RELATED APPLICATION

The present application claims priority of U.S. Provisional Appl. No. 63/493,249 filed Mar. 30, 2023, whose content is hereby incorporated by reference herein in its entirety.

FIELD OF THE INVENTION

The invention is in the field of orthopedic surgery on a body part of a patient, such as the shoulder, in particular the use of mixed reality to assist in the performance of prosthetic surgery, such as orthopedic shoulder prosthesis surgery.

In one aspect, the invention involves a method, system, and computer program for assisting shoulder prosthesis installation, such as piercing of the glenoid along an axis of the glenoid in the scapula, and/or installation of the glenoid component.

BACKGROUND ART

Different techniques have been available to perform piercing of the glenoid along an axis of the glenoid in the scapula.

The preparation of the humerus, as well as the preparation of the rest of the scapula, are typically performed using standard instrumentation, often provided by, or corresponding to requirements by, the manufacturer of the implant to be used. Standards aspects of a typical shoulder prosthesis operating protocol are well known to the person of the art and in the literature.

In this context, the piercing of the glenoid must take into account the shoulder prosthesis (implant) manufacturer's indications and recommendations, the available surgical techniques, and the particular morphology and biomechanical features of the shoulder joint specific to each patient.

Thus, a surgeon performing the implantation of the prosthetic component on the scapula must determine an appropriate compromise among these various parameters, with the objective of obtaining satisfactory clinical results and patient satisfaction. In the case of bad positioning of a prosthetic component, the patient runs many risks, including poor recovery of the joint, operative complications, reduction in the lifespan of the implant, loosening of the component requiring repair or even replacement and/or reimplantation.

According to a traditional protocol, positioning of the implant is planned by the surgical team using two-dimensional x-ray images. The surgeon then chooses the size and positioning of the implant in a single plane, by superimposing on the radiological image a tracing representing the prosthesis. During the surgical procedure, the surgeon then tries to reproduce this positioning using instruments to determine the orientation of the implant in relation to visible anatomical landmarks of the patient.

Typically, for orthopedic shoulder prosthesis surgery, the surgeon would 1) position manually a piercing guide equipped with a positioning flange on the scapula, 2) mark an entry point relative to the positioning flange, 3) perform the piercing of the central hole, and 4) perform machining of the glenoid around the opening of the central hole, guided by the hole.

However, this traditional method, which relies heavily on the surgeon's professional evaluation of positions and orientations relative to visible bone surfaces and anatomical features of the glenoid, does not make it possible to control precisely and reproducibly all the positioning parameters. For example, in the case of shoulder prostheses, it is impossible to visualize the entire scapula based only on the visible portion of the glenoid during the operation. As a result, for a large proportion of prosthetic implants, the positioning is not optimal. Typically, a surgeon of the shoulder would obtain a precision of about ±12° relative to a target positioning. More precisely, the error in the orientation of the scapula component of a shoulder prosthesis relative to a target orientation along an axis of the scapula is one degree or more in a large majority of cases.

In order to assist the surgeon with this aspect of the procedure, implant manufacturers have provided various aiming instruments, ranging from simple mechanical guides to the advanced navigation systems.

For example, in the case of orthopedic shoulder prosthesis surgery, a mechanical piercing guide can be provided, having an assembly portion adapted to bear on a lower edge of the glenoid, and a guiding portion adapted to guide a piercing of the central hole and/or a machining of the glenoid around an opening of the central hole. However, this technique of reducing incorrect positioning and/or orientation is insufficient particularly in some cases such as a disformed or worn scapula.

Another assistance system relies on pre-operative planification of the operation using a 3D visual representation of the surgical scene using scanner and/or RMI imagery. A mobile piercing guide having a plurality of adjustable bearing arms is configured in accordance with values calculated by a planification computer program of the assistance system. The piercing guide is then installed on the glenoid of the patient to guide the piercing operation. However, this technique is dependent on proper calculation of the adjustment values for the piercing guide, which may be affected by errors due to difficulties in accessing articular surfaces, for example caused by the presence of soft tissues. Also, a disformed or worn scapula may make proper use of the piercing guide difficult or even impossible.

Another assistance system similarly relies on pre-operative planification of the operation using a 3D visual representation of the surgical scene, followed by the production of a single-use piercing guide specific to the patient. The single-use piercing guide is positioned on the articular surface of the glenoid, permitting guided piercing through the single-use piercing guide. Although this technique is well-adapted to permit adjustments specific to the particular anatomy of each patient, the reliance on single-use components is costly and wasteful in materials, and the production time causes delays in the performance of the surgery.

Still another assistance system relies on a navigated piercing protocol. A navigation system is installed in proximity to the patient. A reference (navigation) marker is mounted on the coracoid of the patient to permit acquisition of anatomical reference data of the patient by the navigation system. A computer program of the navigation system calculates piercing parameters (surface entry, orientation, etc.). The piercing parameters are displayed on a side screen of the navigation system. A navigated surgical tool, typically a piercing guide, also includes a reference marker permitting acquisition of position and/or orientation values of the surgical tool by the navigation system, allowing the surgeon to verify visually the position and/or orientation of the navigated surgical tool by looking at the side screen of the navigation system. However, this navigation assistance technique requires the surgeon to shift their field of vision between the operating scene and the side screen of the navigation system. In addition, the transmission of positioning and/or orientation and/or imagery data may be hampered and/or interrupted if the surgeon's placement and/or movement interfere spatially or otherwise with the transmission, for example, if a body part of the surgeon is placed between the marker(s) and the navigation system during performance of the surgery. Also, the reference markers usually require replaceable components such as batteries to permit acquisition of positioning and/or orientation data by the navigation system.

SUMMARY OF THE INVENTION

In one aspect, the invention is adapted to assist the performance of an operation on a body part such as the shoulder by combining advantages of preoperative planning, surgical navigation, and visualization, by using mixed reality virtualization.

In another, more specific aspect, the invention is adapted to improve shoulder surgery such as prosthetic surgery, more precisely glenoid drilling during shoulder arthroplasty intervention.

In another aspect, the invention is adapted to permit visualization of a virtual operating scene, or portions of a virtual operating scene, directly in the field of vision of the surgeon performing the surgery, in superposition with an actual virtual operating scene.

In another aspect, the invention is adapted to provide a mixed reality (MR) navigation method, system, and program allowing a surgeon to navigate the piercing of the glenoid during shoulder surgery in accordance to planned data, without interrupting the visual representation of the surgical scene.

In another aspect, the invention is adapted to provide:

- a MR device intended to be worn by a user such as the surgeon performing the operation, and configured to display a virtual surgical scene or portions thereof, and/or
- a computer (integrated into the MR device, or separate) configured to allow adjusting of the positioning of virtual components of the virtual surgical scene, such as the scapula of the patient and/or of surgical tool(s) used by the surgeon, or a computer program adapted to provide corresponding functionalities when executed on a computer, and/or
- dedicated reference marker(s) and/or surgical tool(s) such as a piercing guide, optionally equipped with a reference marker, the computer or program being configured to acquire positioning data from the reference marker(s).

In another aspect, the invention is adapted to provide a method as in points 1-17 below.

1. A method of performing an operation on a body part of a patient using a mixed reality (MR) device worn by a user performing the operation, comprising:
   - providing a visual representation of an operating scene including an anatomical feature of the body part of the patient, wherein the visual representation comprises a virtual anatomical feature representing the anatomical feature of the patient,
   - performing a first adjusting of a position and/or orientation of the visual representation relative to the anatomical feature of the patient, wherein the virtual anatomical feature is in superposition with the anatomical feature of the patient,
   - displaying the visual representation by the MR device worn by the user, wherein the visual representation is displayed in superposition with the anatomical feature of the patient in a field of vision of the user,
   - performing repeated or continuous adjusting the position and/or orientation of the visual representation, wherein, when the MR device worn by the user moves relative to the anatomical feature of the patient, the virtual anatomical feature of the visual representation remains in superposition with the anatomical feature of the patient.
2. The method of point 1, comprising:
   - acquiring successive images of the anatomical feature by a perception device of the MR device worn by the user, and
   - adjusting the position and/or orientation of the visual representation by a display device of the MR device, as a function of the images acquired by the perception device.
3. The method of point 1 or point 2, wherein the first adjusting comprises providing a first reference marker having a set position and/or orientation relative to the anatomical feature of the patient, and performing the first adjusting relative to the first reference marker.
4. The method of point 1 or any of points 2 or 3, wherein the visual representation comprises indications of a target position and/or orientation of a surgical tool intended to be used by the user, and the method further comprises:
   - adjusting a position and/or orientation of the surgical tool as a function of the indications of the target position and/or orientation of the surgical tool.
5. The method of point 4, further comprising:
   - providing a second reference marker on the surgical tool, the second marker having a set position and/or orientation relative to the surgical tool,
   - displaying in the virtual surgical scene an indication of a position and/or orientation of the surgical tool relative to the position and/or orientation of the virtual surgical tool, as a function of the position and/or orientation of the second marker.
6. The method of point 1 or any of points 2 to 5, wherein the first reference marker is a plane marker and/or a monochrome marker.
7. The method of point 1 or any of points 2 to 6, wherein the first adjusting comprises:
   - attaching the first reference marker to the shoulder blade, and
   - adjusting predetermined locations and/or orientations of the visual representation to be superposed with corresponding predetermined positions and/or orientations of the anatomical feature, based on the position and/or orientation of the first reference marker.
8. The method of point 4 or point 5 or the method of point 4 and any of points 6 or 7, wherein the second reference marker is a plane marker and/or a monochrome marker.
9. The method of point 1 or any of points 2 to 8, wherein the body part of the patient is a shoulder, and the visual representation includes a display of a piercing axis in a glenoid of a scapula of the shoulder.
10. The method of point 4 or point 5 or the method of point 4 and any of points 6 to 9, wherein the body part of the patient is a shoulder, and the visual representation includes a display of a piercing axis in a glenoid of a scapula of the shoulder, and the surgical tool is a piercing tool adapted to pierce the glenoid and/or a piercing guide adapted to guide piercing of the glenoid for installation of a shoulder prosthesis.

11. The method of point 10, wherein the display of the piercing axis includes a display of an indication of inclination angle and an indication of anteversion angle.

12. The method of point 10 or point 11, wherein a precision of angular representation of an adequation of orientation of the surgical tool to the piercing axis is equal or less than 1 degree.

13. The method of point 12, wherein the adequation is indicated by color coding, including different colors for angles of more than 1 degree and for angles equal or less than 1 degree, respectively.

14. The method of point 1 or any of points 2 to 13, comprising, before adjusting the visual representation:

registering the user, and receiving an input of information on the patient.

15. The method of point 1 or any of points 2 to 14, wherein the first adjusting of the visual representation comprises:

by the user, identifying a plurality of reference points on the anatomical feature of the patient, and adjusting the virtual anatomical feature of the patient in the visual representation to respective positions and/or orientations of the plurality of reference points of the anatomical feature of the patient.

16. The method of point 15, further comprising:

receiving an input of information about a surgical tool, detecting a position and orientation of the surgical tool.

17. the method of point 1 or any of points 2 to 16, wherein the displaying comprises projecting a 3D visual representation of the visual representation in the field of vision of the user wearing the MR device.

In another aspect, the invention is adapted to provide a system as in points 18-19 below.

18. A mixed reality navigation system for assisting an operation on a body part of a patient performed by a user of the system, the system comprising a mixed reality device worn by the user performing the operation, the mixed reality device comprising:

a computer configured to provide a visual representation of an anatomical feature of the body part of the patient, wherein the visual representation comprises a virtual anatomical feature representing the anatomical feature of the patient, the computer being adapted to perform a first adjusting of a position and/or orientation of the visual representation relative to the anatomical feature of the patient, wherein the virtual anatomical feature is in superposition with the anatomical feature of the patient, the computer being adapted to perform repeated or continuous adjusting of the position and/or orientation of the visual representation, wherein, when the MR device worn by the user moves relative to the anatomical feature of the patient, the virtual anatomical feature of the visual representation remains in superposition with the anatomical feature of the patient, and a display device configured to display the visual representation on the MR device worn by the user, wherein the visual representation is displayed in superposition with the anatomical feature of the patient in a field of vision of the user.

19. The system of point 18, wherein the system is configured to perform the first adjusting of the visual representation, wherein the first adjusting comprises:

receiving respective positions and/or orientation information on a plurality of reference points on the anatomical feature of the patient, and adjusting the virtual anatomical feature of the patient in the visual representation to correspond to the position and/or orientation of the anatomical feature of the patient in the surgical scene.

In another aspect, the invention is adapted to provide a computer program as in point 20 below.

20. A non-transitory storage medium comprising a computer program, wherein the computer program is configured, when the program is executed by a computer of a mixed reality navigation system worn by a user for assisting an operation on a body part of a patient performed by the user, to cause the mixed reality navigation system to:

provide a visual representation of an anatomical feature of the body part of the patient, wherein the visual representation comprises a virtual anatomical feature representing the anatomical feature of the patient, perform a first adjusting of a position and/or orientation of the visual representation relative to the anatomical feature of the patient, wherein the virtual anatomical feature is in superposition with the anatomical feature of the patient, perform repeated or continuous adjusting of the position and/or orientation of the visual representation, wherein, when the MR device worn by the user moves relative to the anatomical feature of the patient, the virtual anatomical feature of the visual representation remains in superposition with the anatomical feature of the patient, and display the visual representation by the MR device worn by the user, wherein the visual representation is displayed in superposition with the anatomical feature of the patient in a field of vision of the user.

BRIEF DESCRIPTION OF THE DRAWINGS

Further aspects of the invention will be described in reference to the appended drawings which illustrate non-limiting exemplary embodiments, among which.

DETAILED DESCRIPTION OF PARTICULAR EMBODIMENTS

Figure 1:
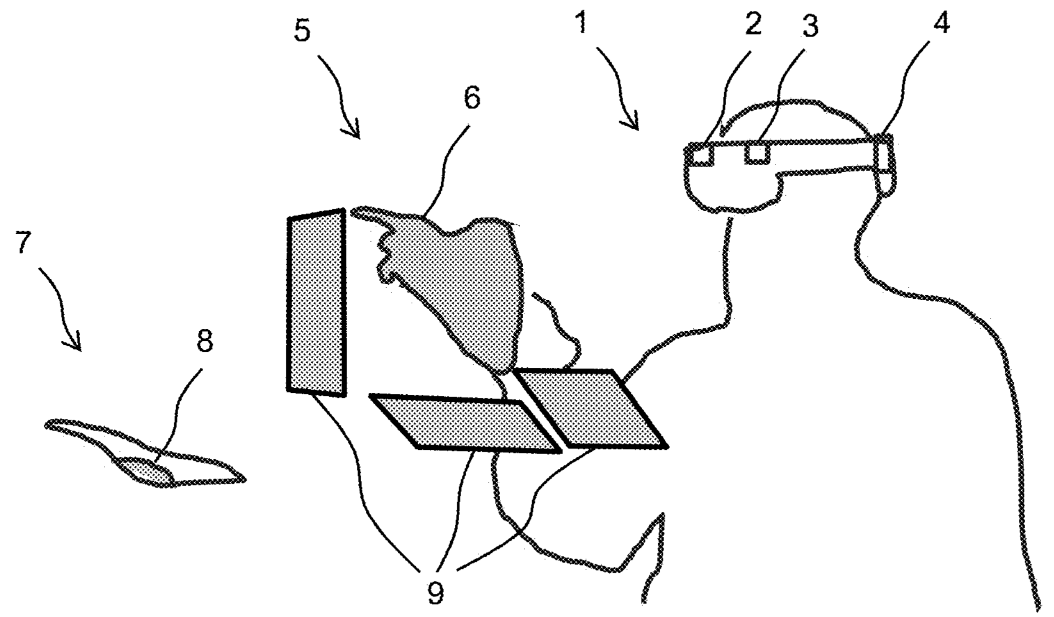
FIG. 1 is a general view of a shoulder prosthetic operating scene showing the MR device worn by the user and an illustrative MR visual representation including a representation of the patient's glenoid, superposed with the actual surgical scene in the field of vision of the surgeon.
Figures 2A, 2B, 2C, 2D, 2E, 2F:
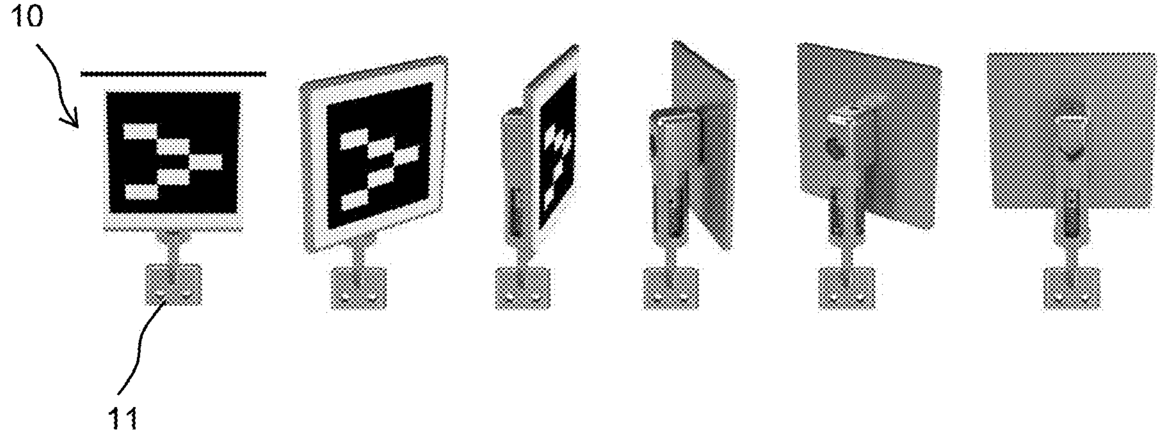
FIGS. 2*a*-2*f* are six views of a reference marker (fiducial marker) which is pre-configurable in different possible orientations.

The following is a description of non-limitative embodiments illustrating aspects of the invention, which can be found alone or in various combinations.

A shoulder prosthesis operation typically uses planification of the intervention carried out using a planification assistance system, such as a system based on pre-operative imaging using an operation planification software such as the ShoulderPlan software from Pixee Medical, or other qualified software.

Initially, a 3D virtual model of the patient's shoulder anatomy, usually obtained from MRIs of the patient, is loaded into the planification system, in order to allow defining the size and placement of different prosthetic components.

The output data of this planification is, for example, in the form of a compressed file in zip format, or any other appropriate format, and includes a 3D model of the patient's scapula, as well as the planned orientation for drilling the glenoid. This file can constitute or be part of the input data during use of the invention in the operating room.

The invention also typically uses reference marker(s), often called fiducial marker(s), which can be simple planar monochrome markers, for example (such as arUco monochrome markers). The markers can be attached to the patient's bone structure and/or to surgical instruments to provide a positioning reference to calculate position and/or orientation values in positioning, and/or calculate translation and/or rotation values in movement.

The data are processed by a computer of the system, and the display is provided by a display device of a mixed reality (MR) device intended to be worn by the user during the operation. The computer can be separate or included in the MR device, which can be, or example, a mixed reality headset of the Microsoft Hololens 2 type, and is advantageously capable of displaying a virtual operating scene directly in the surgeon's field of vision, including virtual graphic elements and positioning (location, orientation . . . ) and/or movement (translation, rotation, direction, speed, acceleration . . . ) values, superimposed in real time on the surgeon's body.

According to an aspect of the invention, the reference marker's data allows the 3D model of the patient's scapula to be virtually attached to the actual bone in the virtual operating scene displayed on the MR device.

Another marker is optionally present on the piercing guide and/or piercing tool, which allows the system to know the position and/or orientation of the piercing guide or tool in relation to the reference marker, and to calculate clinical values useful for the surgeon.

A perception device, such as a RGB camera which can be separate or integrated into the MR device worn by the user, is adapted to track the marker(s) of the surgical tool(s), in order to assist the user by indicating positioning and/or movement values of the surgical tool, and/or by displaying a 3D model of the surgical tool, optionally along with target values and/or target positioning representations of the tool in the displayed scene.

An exemplary planification protocol is as follows.

Typically, the surgical intervention is already in process when the surgeon begins the protocol. Usually, the shoulder joint has been previously exposed and prepared, with its humeral head removed, then the user carries out the registration before the navigation of the glenoid implant axis.

The registration process is carried out to virtually position the digital 3D model of the patient's anatomy in space so that it coincides with the patient's actual bone structure in the field of vision of the surgeon wearing the MR device. To do this, the user points on the actual bone, typically geometric and anatomic referential locations or landmarks which have been pre-defined during an earlier phase of the planification process. The system then executes an algorithm to link points on the 3D model corresponding with those identified on the bone(s) of the patient.

Once the registration has been carried out, the system is able to display, thanks to mixed reality, the virtual model of the scapula superimposed on the patient's bone, as well as the planned drilling axis.

When the user approaches and manipulates the surgical tool within the operating scene, the system is capable of indicating in real time position and/or orientation values, and/or translation and/or rotation values, including optionally by including a 3D model of the surgical tool in the virtual surgical scene, as well as a virtual display of the positioning and movements of the surgical tool, so as to assist the aiming and operative gestures.

For example, appropriate colors may be used in the display, depending on the proximity of the positioning and/or movement values of the surgical tool to the target values set during the earlier planification phase. For example, in a simple embodiment, a virtual representation of the tool registered with the actual tool, or a symbolized representation of the tool or its environment, changes color to indicate proximity of the orientation of the actual tool to a target angle.

Position, orientation, and transformation attributes are in the glenoidal reference frame. Position is a vector associated with the x,y,z components of the planned axis entry point on the glenoid in the glenoid frame of reference. Orientation is the quaternion associated with the planned axis in the glenoid frame of reference.

The glenoidal reference frame is already pre-established in the planification platform. The position and rotation of the scapula node make it possible to create a transformation matrix that determines the geometric transformation between the segmentation frame of reference and the glenoid frame of reference. Translation corresponds to the data contained in a position attribute. Rotation corresponds to the data contained in an orientation attribute. For example, the transformation matrix of the baseplate can be calculated in the glenoid reference frame with the position and orientation in the baseplate node. These data are those of the position, version and inclination planning established by the surgeon.

The navigated inclination can be defined as the angle between the axis of the drill guide and the line of the supraspinatus fossa. The navigated inclination can be calculated from a director vector representing the drill guide axis, and a director vector representing the line of the supraspinous fossa, taken in a same frame of reference, for example, the glenoidian reference frame.

The navigated version can be defined as the calculation of the angle between the drill guide axis and the vector normal to the coronal plane. The navigated version can be calculated from a director vector representing the drill guide axis, and a normal vector to the coronal plane, taken in a same frame of reference, for example, the glenoidian reference frame. The version the user sees is therefore the angle of the drill guide axis in the glenoid reference frame in the axial plane, which can easily be compared with the planned version displayed.

Thus, in order to better visualize the discrepancies between navigated and planned values, a color system can be implemented: for example, within 1° or 1.5 mm the axis and/or tool contour will be green, between 1° and 2°, or between 1.5 mm and 3 mm, the axis or contour will be yellow, and over 2° or over 3 mm the axis or contour will be red. If the drill guide marker is not visible, the axis and/or tool contour will be in blue. Instead of the whole contour, a contour of only a portion of the tool can be in the specified color.

At least in some embodiments or aspects of the invention, the invention allows adjustment of the 3D model to the particular patient's anatomy during the planification phase, and navigation in real-time of surgical instruments such as the piercing guide during the operative phase, while ensuring permanent superposition of the virtual surgical scene over the actual surgical scene in the field of vision of the user during a relevant portion of the operation, as well as providing positioning (position, orientation . . . ) and/or movement (translation, rotation . . . ) data useful to the surgeon, such as target data and/or data on positioning and/or movement adequation to the target data. In particular, the superposition within the field of vision of the user is maintained during movements of the surgeon, such as head movements during performance of the surgery by a surgeon wearing a MR device of the system on their head.

Accordingly, a simple and cost-effective manner of acquiring target values useful for a surgical intervention, such as a position and angular parameters of glenoid piercing in shoulder prosthesis surgery, is provided. The initial positioning values can be acquired using a simple reference marker fixed to the scapula or successively disposed on remarkable anatomical features of the scapula, without requiring consumables such as battery for the markers. The linking of the 3D model of the anatomy features of the patient in the virtual surgical scene to the actual anatomy features of the patient in the actual surgical scene allows the user to benefit from consistent superposition of the virtual surgical scene over the actual surgical scene, for example, by permitting secure control and monitoring of the position and movements of surgical instruments by user.

Thanks to the MR device worn by the user, the use of a side camera, side screen, and/or side display of a virtual surgical scene or 3D model of the patient's anatomy to the side of the surgeon performing the surgery can be avoided, if desired. Thus, distracting side viewing on a side screen or a side display away from the field of vision toward the area of the surgery can be avoided, and potential shadows or loss of display capability by the passage of obstacles between the marker and the perception device can also be avoided.

A software platform for running a program implementing an embodiment of the present invention includes for example some or all of the features described below.

A person/machine interface allows registering of the surgical procedure, the patient, and/or the user, typically the surgeon. A surgical tool and/or surgical tool set can also be registered. Physical embodiments of the interface can include a display, buttons, keyboard(s), and/or a touch screen, for example, which can be integrated into, attached to, or separate from the MR device.

Patient data is accessed and/or uploaded to the platform. For example, after selecting the data for the desired patient, the user has access to a validation interface where the information on the patient and/or a 3D model of the patient's anatomy at the shoulder area is capable of being accessed and/or uploaded.

Similarly, instrument data can be accessed and/or uploaded to the platform, such as a QR code identifying the surgical tool or toolset to be used by the surgeon during the surgery.

Alternatively, the patient data and/or instrument data can be pre-set in the system before the user starts using the system. Examples of an instrument kit is ShoulderTools Instrument Kit by Pixee Medical, which is adapted to be used with a navigation system managed by the ShoulderPlus software by Pixee Medical.

Before performing the surgical operation, the user must perform a first acquisition of anatomical features of the patient, including landmark position, for example; at least one, or at least two, or at least three, or at least four, or even all of the following: superior glenoid, posterior glenoid, anterior glenoid, lower glenoid and/or tip of the coracoid, and/or landmark surfaces, for example, at least one, or both of the following: glenoid, coracoid.

A progress bar can be displayed to show advancement and/or completion of the acquisition. Detection criteria can be defined to assist the user during the acquisition, which can be conveyed by text messages and/or illustrations, as managed by the planning software, for example, such as the ShoulderPlus software in the case of a ShoulderTools instrument kit, these text messages and/or illustrations being displayed on the display of the MR device worn by the user, or on a separate screen.

A validation screen can be displayed to the user. Acquisition data may be displayed, optionally with adequation codes representing adequation between the virtual anatomical features on the virtual model and the actual anatomical features on the patient, for example, with coded colors on the acquisition surfaces or otherwise. The user can be provided with an opportunity to register the completed 3D model and/or to redo certain points or acquisition routines of the 3D model's creation, positioning and/or linking to the actual anatomical feature(s) of the patient.

Further, target data of the planned operation can be displayed in the field of vision of the user, such as the planned drilling axis of the scapula for the shoulder prosthesis operation, along with additional data, for example, location and/or movement of a surgical tool such as a piercing tool manipulated by the user. The target data such as data on the planned drilling axis can be calculated during initialization or loaded into the computer before or during initialization.

For example, the user acquires five landmarks by placing the tip of a pointer on the landmarks, while the system is detecting the reference markers of the scapula and of the pointer, respectively. Similarly, the user can acquire the surface of the glenoid and/or the coracoid by placing the tip of the pointer on the surface.

When the virtual model of the patient's anatomy has been linked to the actual anatomy of the patient, the virtual model displayed in the field of vision of the user by the MR device remains superposed with the actual anatomy of the patient, including when the user and/or the patient moves in a manner that shifts the user's field of vision relative to the patient, and/or when an instrument manipulated by the user or another person moves within the field of vision of the user.

Accordingly, the system allows the user to improve positioning and/or movement of the surgical tool by adjusting it/them to a target position and/or orientation and/or translation and/or rotation, represented by target values or a target image on the displayed virtual surgical scene in the field of vision of the user. Specifically, the user can adjust an angle of a piercing tool to a target piercing angle and a target entry point at the scapula. The piercing axis includes inclination angle and anteversion angle.

During performance of the surgical operative gesture, such as drilling in the scapula using a drilling tool, control values regarding the target hole, the surgical tool, or both (e.g., angular orientation, distance, etc.), are displayed via the graphical interface.

For example, the visual interface can allow the user to navigate the drill axis of the drilling tool by reproducing a previous planning data and trying to match the planning axis with the instrument axis, or by navigating directly the instrument axis, without planning axis. Navigation values can be displayed: typically, tilt and version are displayed in the field of vision of the user, next to the superposition of the virtual scapula and actual scapula.

A color indicator for the angles and the entry point from the drill axis can be displayed to assist the surgeon.

When the position is considered satisfactory, the user drills the glenoid surface by using adequate instrumentation, such as standard instrument guiding (motor, pins), for example. When a drilling guide has been positioned, the drilling follows the direction set by the drilling guide. The user is now able to control the drill axis control values (e.g., tilt, version, distance from the entry point) are displayed through the graphical interface.

Following performance of the surgical gesture, a report can be downloaded, sent, or otherwise retrieved from the system.

Compared to previous navigation systems for shoulder prostheses, for example those that perform 3D tracking of instruments thanks to an infrared camera positioned close to the operating field, the invention makes it possible to achieve a more secure 3D tracking of surgical instruments, for example, by using the perception device (e.g, RGB and/or infrared camera) of the system. Situations where the markers of the instruments are not visible to the perception system are minimized or avoided, because obstacles typically do not come between the camera and the markers. Thus, the surgeon can avoid having to monitor their own movement or the movements of other persons present in the operating scene to ensure that obstacles do not come in-between the markers and the field of perception of a camera.

Compared to existing navigation systems for shoulder prostheses which display their information on a side screen in the operating room, the use of the MR device makes it possible to display clinical information directly in the field of vision of the user toward the actual operating scene, more precisely in the surgeon's field of vision, superimposed on the patient's anatomy. This has notably the advantage of allowing the surgeon to remain focused on the operating scene and on the patient, in contrast to existing systems with side screen, which require the surgeon to look away and to alternate attention to the surgical scene and attention to the side screen.

Additionally, the superposition gives the surgeon a better appreciation of distances and/or orientations and/or movements, because the mixed reality platform, thanks to its stereoscopic display, allows the perception of 3D, in particular of depth, whereas on existing systems with a side screen, the surgeon must analyze different points of view on the side screen.

The mixed reality display can be a Hololens 2 system mentioned above, or other available commercial products which can be used or adapted for use in the present invention, at least in some embodiments, such as Magic Leap 2, or MR glasses with external CPU, such as NReal Light, XVisio SeerLens, Digilens VI, Jorjin J7EF, Lenovo Thinkreality, etc. Various visualization platforms are also available.

For acquisition of position values and tracking of the surgical scene, a perception device such as a camera can be used, for example, a stereoscopic camera such as Microntracker camera, or medical grade infrared tracking camera, such as an Atracsys or NDI camera. The camera can be black and white, or color. Further, multi-sensor tracking devices that can combine color, infrared, and depth sensors.

According to a preferred aspect of the invention, the user is invited to enter anatomical features such as anatomical landmarks and/or surfaces, using an instrument navigated directly on the articular surface of the patient's scapula. In practice, the user can for example manipulate a pointer equipped with a reference marker, by placing the pointer at various locations on the patient's bones or other features, to collect coordinates in 3D as part of the 3D model of the patient's anatomy, which, subsequently or in real time, are matched with the actual locations in the patient's anatomy present in the actual surgical scene, so that the computer can use this first adjustment to continue maintaining sufficient anatomical features or points of the 3D model superposed with the actual features or points of the actual anatomy of the patient in the actual surgical scene.

Alternatively, or in addition to a reference pointer, a 3D scanner, such as a hand-held scanner equipped with a navigation marker, can be navigated by the user.

In a simple embodiment, the invention allows improving the positioning in real time of a piercing guide or piercing tool, according to an orientation matching a target axis in relation to the scapula of the patient.

A navigated or non-navigated drill can be manipulated following placement and validation of the orientation of a piercing guide using the method or system of the invention. Instrumentation for a precise navigated total shoulder prosthesis protocol is designed to identify anatomical landmarks on the scapula of the patient, as well as the precise orientation of a piercing axis in order to guide a piercing tool to create a hole inside the glenoid. For this purpose, the instruments can be coupled with tracking markers. For example, ShoulderTools instruments by Pixee Medical are adapted for tracking using ShoulderPlus software, also by Pixee Medical, allowing tracking of their position and orientation during surgery, performance of various geometric calculations, and providing the surgeon with relevant values useful during the surgical procedure. The instruments are advantageously specifically designed to integrate reference markers, such as planar or 3D fiducial markers. The fiducial markers can be simple passive position markers, such as planar monochrome markers.

A reference marker(s) for anatomical feature(s) on the patient, typically the patient's bone structure, more particulary the scapula, can be intended to be rigidly attached to or positioned on the patient's scapula and to serve as a geometric reference for the operations of registration of the 3D model and navigation of the axis of inclination. The rigid attachment of the marker to the bone can be via screws or surgical pins, or it can be by clamping, for example. In a specific embodiment, the instrument includes a planar and/or monochrome 3D location marker of the ArUco type, optionally provided with a mechanism allowing the plane marker to take a plurality of marker orientation positions, for example, so as to enable the user to use the same instrument to operate on the right shoulders and the left shoulders, and/or to set up the most appropriate orientation for the need of the particular surgical scene.

The piercing guide or piercing tool can also be provided with a simple and/or monochrome marker, or another type of fiducial marker, such as an ArUco marker. Several markers of different types can be used together as appropriate to optimize operation of the system.

For example, ArUco type planar markers can be replaced or combined by any other type of markers, specific to the 3D localization system used in the execution platform: planar markers other than the ArUco type, passive or active infrared markers, 3D markers, or a combination of the options presented.

The reference marker(s) can be attached to the scapula, or clasped, other positioned in a fixed or temporary manner on the various anatomical features.

In a variant, the piercing guide or piercing tool can be used as a pointer, for example, thanks to the addition of a dedicated end piece for taking anatomical landmarks on the patient's scapula. In an embodiment, the orientation of a handle of the piercing guide can be modified according to the user's preferences. For example, the geometry of the surgical tool can be adapted so that visibility of the marker by the execution platform (carried on the surgeon's head) is ensured, whatever the operated side and the hand (right or left) used by the user.

In the non-limitative embodiments shown in the drawings:

FIG. 1 is a general view of an operating scene showing the mixed reality (MR) device 1 worn by the user, comprising a perceptive device 2 such as a RGB and/or infrared camera, a display device 3 such as a holographic projector, and a computer 4. An illustrative MR visual representation 5 of a virtual surgical scene is projected by the display device 3 and includes a 3D model 6 of the patient's scapula or portion of scapula, superposed into the field of vision of the surgeon over the actual surgical scene 7 including the actual scapula 8. Additional data display fields 9 are included in the MR display to display positioning and/or movement information, for example.

FIGS. 2*a*-2*f* are views of a reference marker 10 designed to be fixed on the scapula by a flange 11. The flange has holes for the passage of surgical pins. The reference marker 10 is intended to allow the perceptive device 2 of the MR device 1 to identify the positioning (location and/or orientation . . . ) and/or movement (translation and/or rotation . . . ) of the scapula. The reference marker 10 is configurable into different orientations of the marker surface relative to the fixation flange 11.

Figure 3:
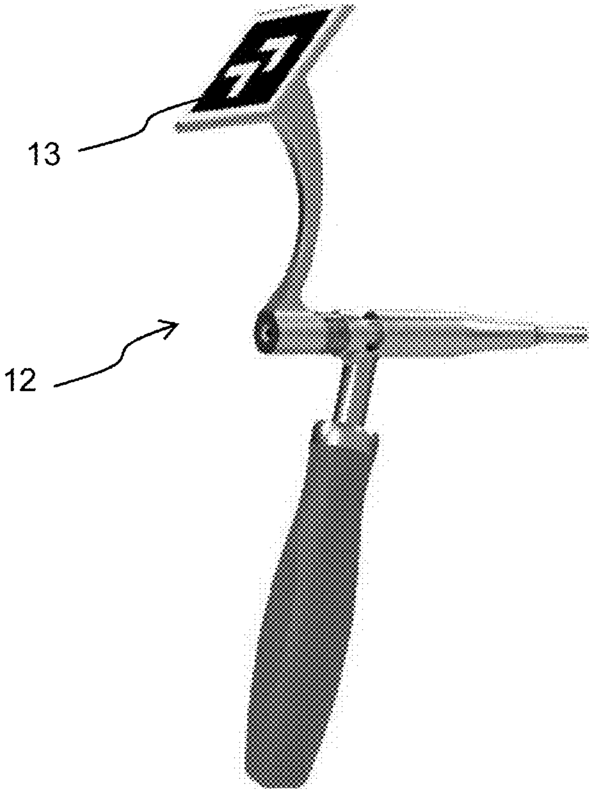
FIG. 3 is a view of a shoulder drill guide bearing a reference marker (fiducial marker).

FIG. 3 is a view of a drill guide 12 bearing a reference marker 13. The reference marker 13 is intended to allow the perceptive device 2 of the MR device 1 to identify the positioning (location and/or orientation . . . ) and/or movement (translation and/or rotation . . . ) of the drill guide. The reference marker 13 is configurable into different orientations of the marker surface relative to the rest of the drill guide 12.

Figure 4:
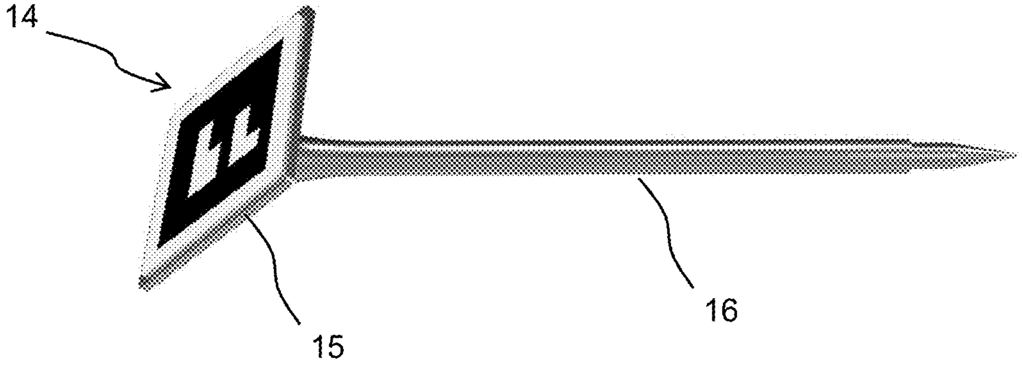
FIG. 4 is a view of a long pointer bearing a reference marker (fiducial marker).

FIG. 4 is a view of a long pointer 14, comprising an ArUco type flat navigation marker 15 rigidly assembled with a rigid rod 16. The pointer 14 is intended to be used to take anatomical landmarks on the bony surface of the patient's scapula, as an optional alternative or supplementation to the reference marker to be fixed on the scapula, which allows the software to align the virtual model of the bone with the real anatomy of the bone. The pointer 14 is completely rigid and contains no mechanism. As an alternative to a dedicated pointer, a drilling guide can also be adapted to be used as pointer.

Figure 5A:
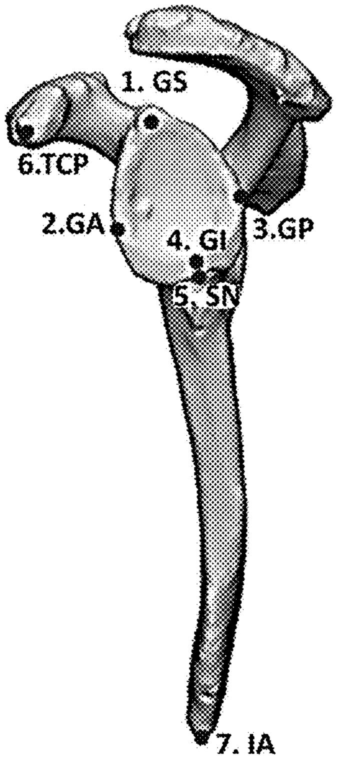
FIG. 5*a* is a side view of a scapula showing landmark points useful in performing adjustment of a virtual scapula of a virtual surgical scene according to the invention.

FIG. 5*a* is a side view of a scapula showing landmark points useful in performing adjustment of a virtual scapula of a virtual surgical scene according to the invention.

Figure 5B:
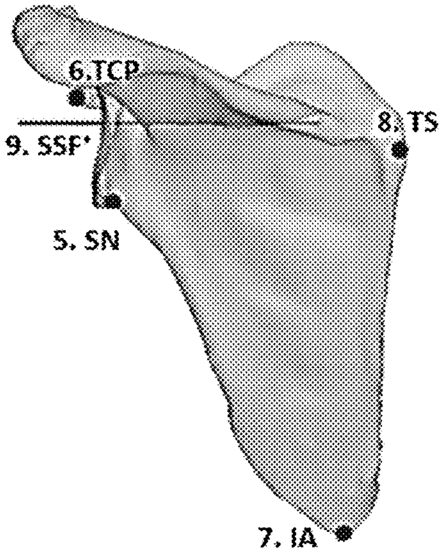
FIG. 5*b* is a front view of a scapula showing landmark points useful in performing adjustment of a virtual scapula of a virtual surgical scene according to the invention.

FIG. 5*b* is a front view of a scapula showing landmark points useful in performing adjustment of a virtual scapula of a virtual surgical scene according to the invention.

For example, landmark points for aligning the virtual model on the view of the actual anatomy of the patient can be selected among the following points:

GS/1: Most superior point of glenoid fossa
GA/2: Most anterior point of glenoid fossa
GP/3: Most posterior point of glenoid fossa
GI/4: Most inferior point of glenoid fossa
SN/5: Intersection between the most lateral point of infraglenoid tubercle and lateral border of the scapula
TCP/6: tip of coracoid process
IA/7: Inferior angle
TS/8: Trigonum spinae
SSF'/9: Supraspinous fossa line (best-fit line in the deepest part of the supra spinatus fossa)

Advantageously, at least two, or at least three, or at least four, or at least five, or at least six, or more of the points can be used.

Figure 6A:
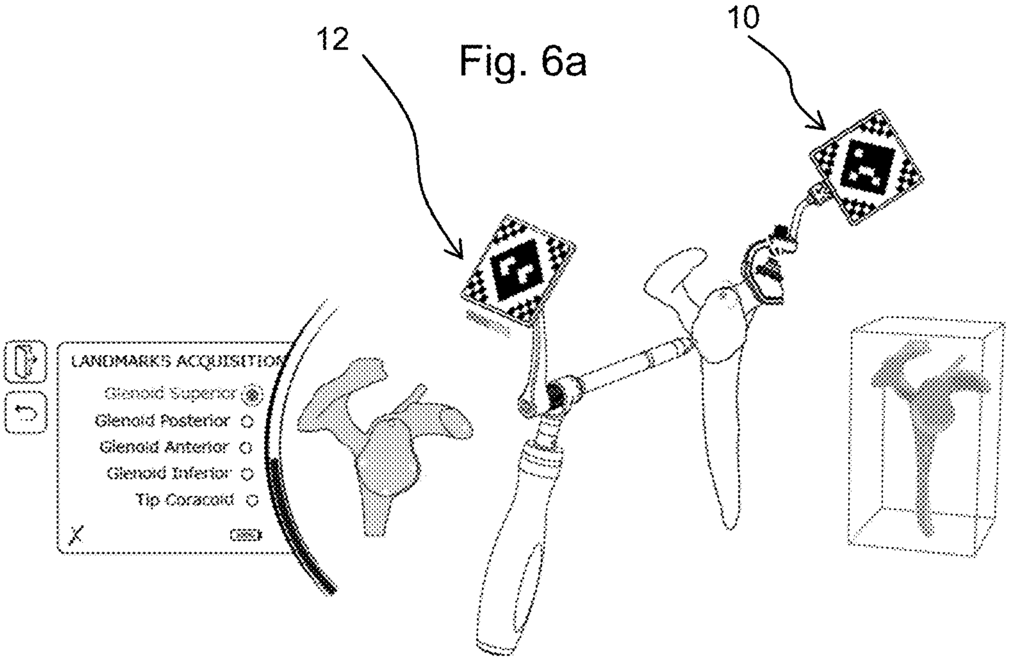
FIG. 6*a* is a view of a virtual surgical scene including a virtual scapula superposed over the actual scapula of the actual surgical scene, during acquisition of landmark points on the actual scapula.

FIG. 6*a* is a view of a virtual surgical scene including a virtual scapula superposed over the actual scapula of the actual surgical scene, during acquisition of landmark points on the actual scapula, such as glenoid superior, glenoid posterior, glenoid anterior, glenoid inferior, tip coracoid, to register the corresponding landmark points on the virtual scapula of the virtual surgical scene, so as to calculate the parameters that will ensure the initial superposition and maintenance of the superposition during movements of the surgeon.

Figure 6B:
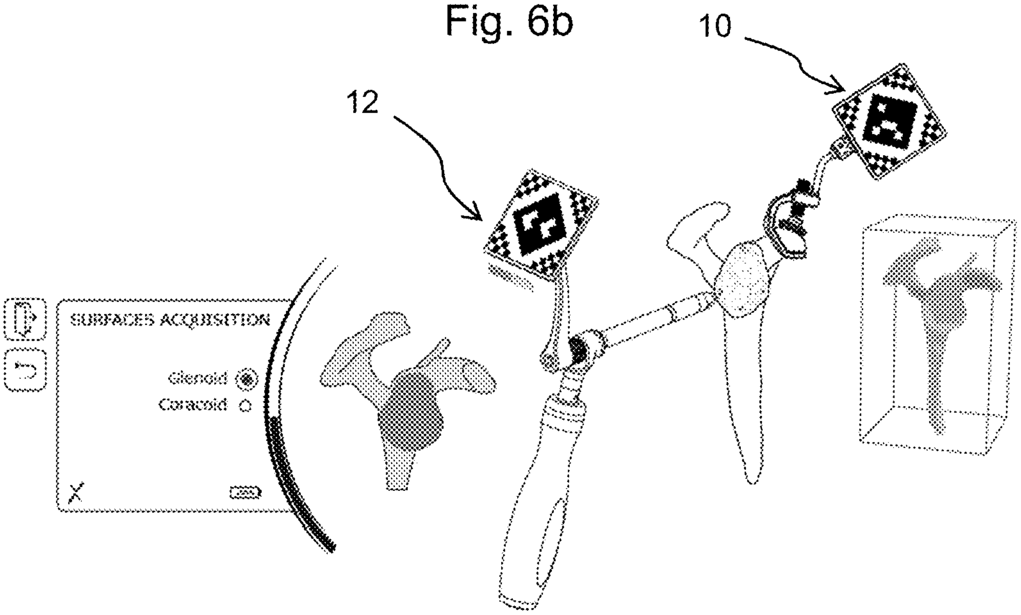
FIG. 6*b* is a view corresponding to the view of FIG. 6*a*, during acquisition of landmark surfaces of the scapula, such as glenoid and/or caracoid.

FIG. 6*b* is a view corresponding to the view of FIG. 6*a*, during acquisition of landmark surfaces of the scapula, such as glenoid and/or caracoid.

Figure 7A:
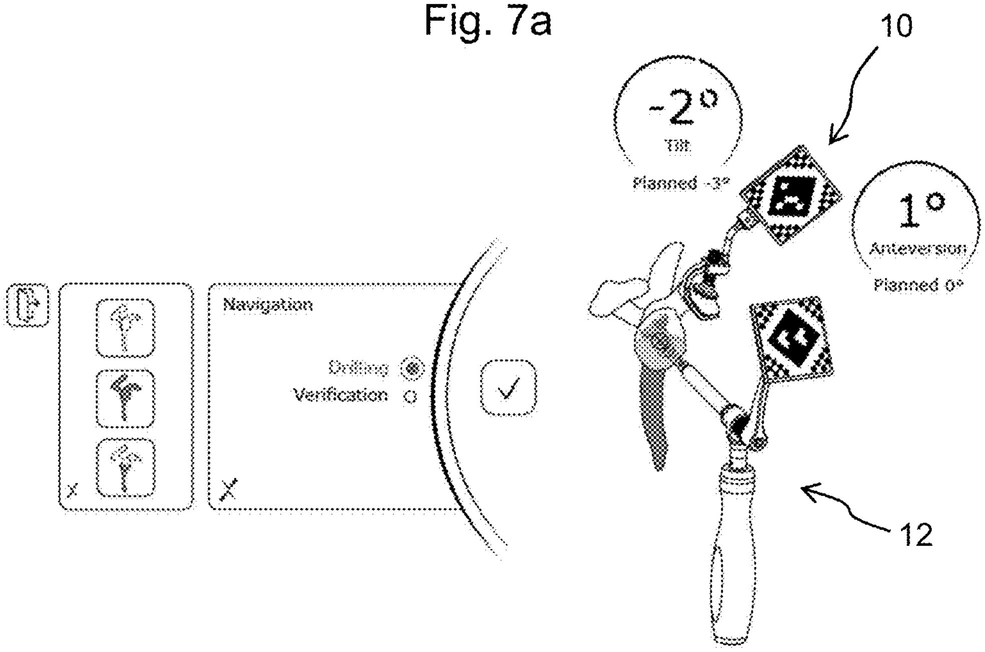
FIG. 7*a* is a view of the virtual surgical scene including a virtual scapula superposed over the actual scapula of the actual surgical scene, showing adjustment of the position of the drilling tool relative to a target position indicated on the virtual surgical scene, during a drilling phase.

FIG. 7*a* is a view of the virtual surgical scene including a virtual scapula superposed over the actual scapula of the actual surgical scene, showing adjustment of the position of the drilling tool relative to a target position indicated on the virtual surgical scene, during a drilling phase.

Figure 7B:
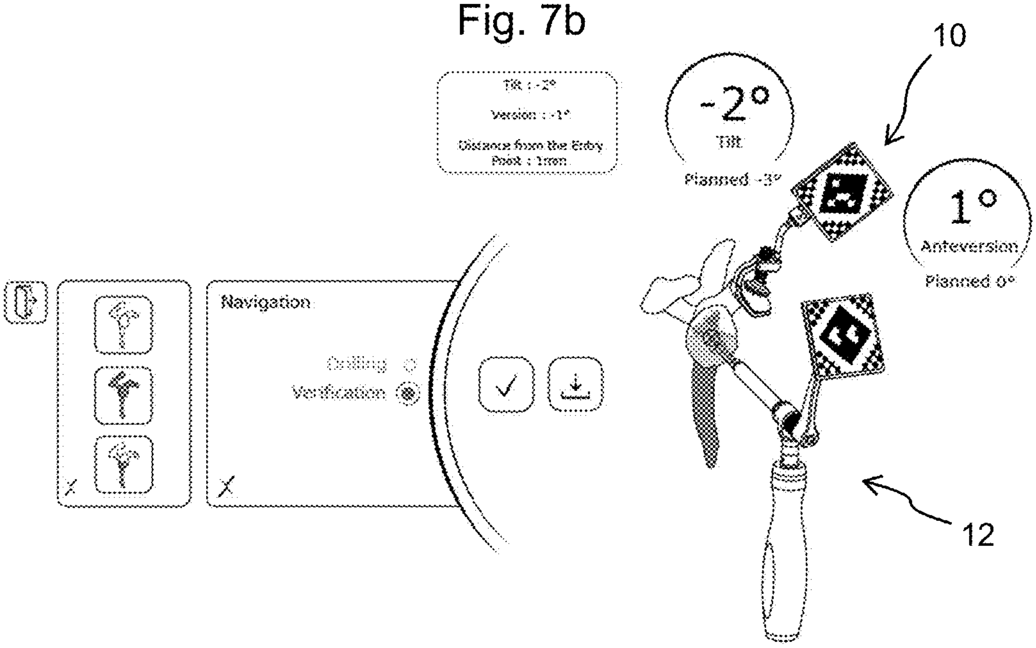
FIG. 7*b* is a view corresponding to the view of FIG. 7*a*, during a verification phase after drilling.

FIG. 7*b* is a view corresponding to the view of FIG. 7*a*, during a verification phase after drilling.

In the field of vision of the user, indications of tilt angle and anteversion angle are provided, as well as optionally position of the drilling tip. The virtual scapula remains superposed over the actual scapula in the field of vision of the user during the drilling process, and the angles indications are also continuously provided in the field of vision of the user. Thus, the surgeon can monitor and manipulate the use of the drilling tool to optimize the location and orientation of the drilling tool.

The mixed reality visual representation can be a 2D image or superposition of 2D images with superposed information, or a 3D model including superposed information provided by the device, or even a virtual 3D simulation of an actual view with superposed information, or any combination and/or juxtaposition of these mixed reality views. The virtual simulation of an actual view can be created based on an actual view, on a model, such as a 2D or 3D model, of the actual view, from a predefined model, such as a 2D or 3D model, or on any combination of these simulations. Portions of an actual view or of an image of an actual view may be excluded or occluded in favor of the mixed reality information, such as by framing and/or covering.

Maintenance of superposition during movements of the surgeon means that the virtual scapula remains within 10 degrees, preferably within 5 degrees, preferably with 4, 3, 2, or even 1 degree of the actual scapula in the field of vision of the user wearing the MR device and/or in the field of vision of a perception device carried by the MR device.

The above disclosures, embodiments and examples are nonlimitative and for illustrative purposes only. The above non-limiting illustrations of the invention include exemplary embodiments of the invention described in the context of an application for the shoulder prosthesis surgery. Applications of the invention are not limited to any particular type of surgical operation, on any portion of the body of any type of human or other animal patient. The invention finds application in other surgical circumstances as well as in other fields.

The invention claimed is:

1. A method of performing an operation on a body part of a patient using a mixed reality (MR) device worn by a user performing the operation, wherein the user performing the operation uses a surgical tool, comprising:

providing a visual representation of an operating scene including an anatomical feature of the body part of the patient, wherein the visual representation is displayed by the MR device to the user, wherein the visual representation comprises 1) a virtual anatomical feature representing the anatomical feature of the patient, and 2) indications of a target position and/or orientation of the surgical tool, so that the user can adjust a position and/or orientation of the surgical tool as a function of the indications of the target position and/or orientation of the surgical tool, performing a first adjusting of a position and/or orientation of the visual representation relative to the anatomical feature of the patient, wherein the virtual anatomical feature is in superposition with the anatomical feature of the patient, so that the visual representation is displayed to the user in superposition with the anatomical feature of the patient in a field of vision of the user, acquiring successive images of the anatomical feature by a perception device of the MR device, and performing repeated or continuous adjusting of the position and/or orientation of the visual representation as a function of the successive images, wherein, when the MR device worn by the user moves relative to the anatomical feature of the patient, the virtual anatomical feature of the visual representation remains in superposition with the anatomical feature of the patient, and updating in real time the indications of the target position and/or orientation of the surgical tool in the visual representation in superposition with the anatomical feature of the patient.

2. The method of claim 1, wherein the first adjusting comprises providing a first reference marker having a set position and/or orientation relative to the anatomical feature of the patient, and performing the first adjusting relative to the first reference marker.

3. The method of claim 1, further comprising adjusting in real time, by the user, a position and/or orientation of the surgical tool as a function of the real time updates of the indications of the target position and/or orientation of the surgical tool.

4. The method of claim 1, further comprising:

providing a second reference marker on the surgical tool, the second marker having a set position and/or orientation relative to the surgical tool, displaying in the virtual surgical scene an indication of a position and/or orientation of the surgical tool relative to the position and/or orientation of the virtual surgical tool, as a function of the position and/or orientation of the second marker.

5. The method of claim 1, wherein the first reference marker is a plane marker and/or a monochrome marker.

6. The method of claim 1, wherein the first adjusting comprises:

attaching the first reference marker to the shoulder blade, and adjusting predetermined locations and/or orientations of the visual representation to be superposed with corresponding predetermined positions and/or orientations of the anatomical feature, based on the position and/or orientation of the first reference marker.

7. The method of claim 1, wherein the second reference marker is a plane marker and/or a monochrome marker.

8. The method of claim 1, wherein the body part of the patient is a shoulder, and the visual representation includes a display of a piercing axis in a glenoid of a scapula of the shoulder.

9. The method of claim 1, wherein the body part of the patient is a shoulder, and the visual representation includes a display of a piercing axis in a glenoid of a scapula of the shoulder, and the surgical tool is a piercing tool adapted to pierce the glenoid and/or a piercing guide adapted to guide piercing of the glenoid for installation of a shoulder prosthesis.

10. The method of claim 9, wherein the display of the piercing axis includes a display of an indication of inclination angle and an indication of anteversion angle.

11. The method of claim 9, wherein a precision of angular representation of an adequation of orientation of the surgical tool to the piercing axis is equal or less than 1 degree.

12. The method of claim 11, wherein the adequation is indicated by color coding, including different colors for angles of more than 1 degree and for angles equal or less than 1 degree, respectively.

13. The method of claim 1, comprising, before adjusting the visual representation:

registering the user, and receiving an input of information on the patient.

14. The method of claim 1, wherein the first adjusting of the visual representation comprises:

by the user, identifying a plurality of reference points on the anatomical feature of the patient, and adjusting the virtual anatomical feature of the patient in the visual representation to respective positions and/or orientations of the plurality of reference points of the anatomical feature of the patient.

15. The method of claim 14, further comprising:

receiving an input of information about a surgical tool, detecting a position and orientation of the surgical tool.

16. The method of claim 1, wherein the displaying comprises projecting a 3D visual representation of the visual representation in the field of vision of the user wearing the MR device.

17. A mixed reality navigation system for assisting an operation on a body part of a patient performed by a user of the system, the system comprising a mixed reality device worn by the user performing the operation, wherein the user performing the operation uses a surgical tool, the mixed reality device comprising:

a computer configured to provide a visual representation of an anatomical feature of the body part of the patient, wherein the visual representation is displayed by the MR device to the user, wherein the visual representation comprises 1) a virtual anatomical feature representing the anatomical feature of the patient, and 2) indications of a target position and/or orientation of the surgical tool, so that the user can adjust a position and/or orientation of the surgical tool as a function of the indications of the target position and/or orientation of the surgical tool, the computer being adapted to perform a first adjusting of a position and/or orientation of the visual representation relative to the anatomical feature of the patient, wherein the virtual anatomical feature is in superposition with the anatomical feature of the patient, the computer being adapted to acquire successive images of the anatomical feature by a perception device of the MR device, and perform repeated or continuous adjusting of the position and/or orientation of the visual representation as a function of the successive images, wherein, when the MR device worn by the user moves relative to the anatomical feature of the patient, the virtual anatomical feature of the visual representation remains in superposition with the anatomical feature of the patient, the computer being adapted to update in real time the indications of the target position and/or orientation of the surgical tool in the visual representation in superposition with the anatomical feature of the patient, and a display device configured to display the visual representation on the MR device worn by the user, wherein the visual representation is displayed in superposition with the anatomical feature of the patient in a field of vision of the user, and wherein the indications of the target position and/or orientation of the surgical tool are updated in real time in the visual representation in superposition with the anatomical feature of the patient.

18. The system of claim 17, wherein the system is configured to perform the first adjusting of the visual representation, wherein the first adjusting comprises:

receiving respective positions and/or orientation information on a plurality of reference points on the anatomical feature of the patient, and adjusting the virtual anatomical feature of the patient in the visual representation to correspond to the position and/or orientation of the anatomical feature of the patient in the surgical scene.

19. A non-transitory storage medium comprising a computer program, wherein the computer program is configured, when the program is executed by a computer of a mixed reality navigation system worn by a user for assisting an operation on a body part of a patient performed by the user, wherein the user performing the operation uses a surgical tool, to cause the mixed reality navigation system to:

provide a visual representation of an anatomical feature of the body part of the patient, wherein the visual representation comprises 1) a virtual anatomical feature representing the anatomical feature of the patient, and 2) indications of a target position and/or orientation of the surgical tool, so that the user can adjust a position and/or orientation of the surgical tool as a function of the indications of the target position and/or orientation of the surgical tool, perform a first adjusting of a position and/or orientation of the visual representation relative to the anatomical feature of the patient, wherein the virtual anatomical feature is in superposition with the anatomical feature of the patient, acquire successive images of the anatomical feature by a perception device of the MR device, and perform repeated or continuous adjusting of the position and/or orientation of the visual representation as a function of the successive images, wherein, when the MR device worn by the user moves relative to the anatomical feature of the patient, the virtual anatomical feature of the visual representation remains in superposition with the anatomical feature of the patient, update in real time the indications of the target position and/or orientation of the surgical tool in the visual representation in superposition with the anatomical feature of the patient, and display the visual representation by the MR device worn by the user, wherein the visual representation is displayed in superposition with the anatomical feature of the patient in a field of vision of the user, and wherein the indications of the target position and/or orientation of the surgical tool are updated in real time in the visual representation in superposition with the anatomical feature of the patient.

* * * * *